United States Patent [19]

Hahn et al.

[11] Patent Number: 5,144,064

[45] Date of Patent: Sep. 1, 1992

[54] PREPARATION OF J-ACID UREA

[75] Inventors: Erwin Hahn, Heidelberg; Udo Mayer, Frankenthal; Friedrich-Wilhelm Raulfs, Limburgerhof; Ulrike Schloesser, Mannheim, all of Fed. Rep. of Germany

[73] Assignee: BASF Aktiengesellschaft, Ludwigshafen, Fed. Rep. of Germany

[21] Appl. No.: 764,359

[22] Filed: Sep. 23, 1991

[30] Foreign Application Priority Data

Jun. 20, 1991 [DE] Fed. Rep. of Germany ....... 4120366

[51] Int. Cl.$^5$ .......................................... C07B 273/00
[52] U.S. Cl. .................................................. 562/49
[58] Field of Search ............................ 562/48, 117, 49

[56] References Cited

U.S. PATENT DOCUMENTS 675,631  6/1901  Israel et al. ............................ 562/49
4,599,203  7/1986  Conrow et al. ........................ 562/49

Primary Examiner—Jose G. Dees
Assistant Examiner—Keith D. MacMillan
Attorney, Agent, or Firm—Oblon, Spivak, McClelland, Maier & Neustadt

[57] ABSTRACT

J-Acid urea of the formula

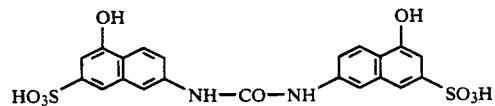

is prepared by reacting 7-amino-4-hydroxynaphthalene-2-sulfonic acid (J-acid) with urea at from 100° to 140° C. under a pressure ranging from atmospheric pressure to 10 bar in an inert solvent to a partial extent, precipitating unconverted J-acid in an acidic medium and separating it off, and, if desired, isolating J-acid urea from the resulting neutralized solution by salting out.

12 Claims, No Drawings

PREPARATION OF J-ACID UREA

The present invention relates to a novel process for preparing J-acid urea from J-acid (7-amino-4-hydroxynaphthalene-2-sulfonic acid) and urea.

J-Acid urea is customarily prepared by reacting J-acid with phosgene (see for example DE Patent 116,200 or PL Patent 12,691).

It is an object of the present invention to provide a novel process for preparing J-acid urea which avoids the use of phosgene as reagent and whereby the target product is obtained in a simple manner in high yield and purity.

We have found that this object is achieved by preparing J-acid urea of the formula

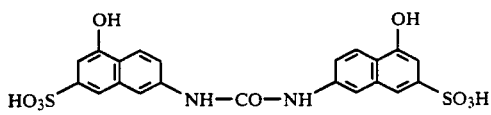

by reacting 7-amino-4-hydroxynaphthalene-2-sulfonic acid of the formula

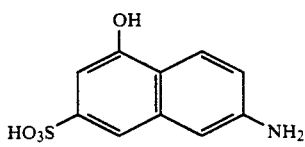

with urea at from 100° to 140° C. under a pressure ranging from atmospheric pressure to 10 bar in an inert solvent to a partial extent, precipitating unconverted J-acid in an acidic medium and separating it off, and, if desired, isolating J-acid urea from the resulting neutralized solution by salting out.

Suitable solvents which can be used in the process of the present invention are for example water, $C_1$-$C_4$-alkanols, such as methanol, ethanol, propanol, isopropanol, butanol, isobutanol or sec-butanol, mixtures of these solvents or dilute aqueous mineral acids, for example 1–5% strength by weight hydrochloric acid, 1–5% strength by weight hydrobromic acid or 1–5% strength by weight sulfuric acid.

The use of water as solvent is preferred.

The process of the present invention is advantageously carried out by charging a suitable apparatus, for example a pressure vessel, with urea, J-acid and solvent. In this initial charge, the molar ratio of urea to J-acid ranges in general from 1:2 to 4:1, preferably being about 1:2. Based on the total weight of J-acid and urea, in general from 30 to 80% by weight, preferably from 50 to 70% by weight, of solvent is used.

The mixture is then heated, generally with stirring, to a temperature within the range from 100° to 140° C., preferably from 110° to 130° C., in particular from 115° to 125° C. At the same time, a pressure is set within the range from atmospheric pressure to 10 bar, preferably from 2 to 6 bar, in particular from 3 to 5 bar. This can be done for example by appropriately adjusting an overflow valve, in which case the ammonia gas formed in the course of the reaction, solvent vapor and also carbon dioxide, formed in minor amounts by decomposition of J-acid urea, can escape.

After a period of from 2 to 40 hours, during which the abovementioned parameters are maintained, the reaction is discontinued and the reaction mixture is cooled down and depressurized.

At this stage the reaction mixture has undergone partial conversion in that in general from 10 to 60%, preferably from 40 to 60%, of the theoretical amount of J-acid urea has been formed.

It is then possible for further solvent, in general from 0 to 30% by weight, based on the total weight of urea and J-acids, to be added.

Thereafter the reaction mixture is admixed with an aqueous mineral acid, for example, 30% strength by weight hydrochloric acid, to set a pH of from 1.5 to 2.5, precipitating unconverted J-acid. It can be separated off, for example by filtering off with suction.

The J-acid thus removed can be reused in the process of the present invention after washing with water and drying.

The filtrate which contains the J-acid urea is then neutralized with a base, for example with from 30 to 50% strength by weight sodium hydroxide or potassium hydroxide solution to a pH of from 5 to 8, preferably about 6.5, and salted out, which can be achieved for example by adding from 30 to 70% by weight of sodium chloride, based on the total weight of J-acid and urea. Thereafter the product is filtered off with suction, dried and, if appropriate, ground.

Using the process of the present invention it is possible to prepare J-acid urea in a simple manner in good yield and in high purity while avoiding the use of phosgene as reactant.

The J-acid urea solution initially obtained in the process of the present invention is sufficiently pure that in suitable cases it can also be used directly.

J-acid urea is a useful intermediate for use as a coupling component in the preparation of azo dyes.

The following example further illustrates the invention:

EXAMPLE 1

In a 4 l stirred vessel, 120 g (2 mol) of urea and 956 g (4 mol) of 7-amino-4-hydroxynaphthalene-2-sulfonic acid (J-acid) in 2000 ml of water are heated to 120° C. in the course of 2 hours and left at that temperature under a pressure of 3.5 bar for 4 hours. After cooling down, the resulting suspension was diluted with water to a total amount of 3300 g and adjusted to pH 2 with 30% strength by weight hydrochloric acid.

The precipitated J-acid was filtered off with suction and washed with water. The pH of the resulting filtrate was lowered to 1.5 using 30% strength by weight hydrochloric acid, precipitating further J-acid, which was combined with the amount obtained above. Drying at 60° C. and subsequent milling left a total of 386 g (37%) of J-acid in the form of a pale gray powder.

The filtrate resulting from separating the J-acid from the reaction mixture was adjusted to pH 6.5 with 50% strength by weight sodium hydroxide solution and saturated with sodium chloride, precipitating the J-acid urea. Filtering off with suction, drying at 60° C. and milling left 600 g (50%) of J-acid urea in the form of a light brown powder having a sodium chloride content of 19% by weight.

EXAMPLE 2

In a 4 l stirred vessel, 120 g (2 mol) of urea and 956 g (4 mol) of 7-amino-4-hydroxynaphthalene-2-sulfonic acid (J-acid) in 2000 ml of water were heated to 120° C. in the course of 2 hours and left at that temperature under a pressure of not more than 8 bar for 4 hours. Following addition of 195 g (0.53 mol) of 10% strength by weight hydrochloric acid and a further 4 hours at 120° C. and not more than 7 bar, the mixture was worked up as described in Example 1.

Altogether this produced 565 g (48%) of J-acid which still contained 13% by weight of J-acid urea, and 454 g (37%) of J-acid urea having a sodium chloride content of 19% by weight.

EXAMPLE 3

In a 4 l stirred vessel, 60 g (1 mol) of urea and 256 g (1 mol) of 7-amino-4-hydroxynaphthalene-2-sulfonic acid (J-acid) in 500 ml of water were refluxed for 16 hours. Following addition of 190 ml of 10% strength by weight hydrochloric acid, 256 g (1 mol) of J-acid and 250 ml of water, refluxing was continued for a further 17 hours.

The workup was carried out as described under Example 1.

Altogether this produced 215 g (35%) of J-acid which still contained 14% by weight of J-acid urea, and 331 g (50%) of J-acid urea having a sodium chloride content of 22% by weight.

We claim:

1. A process for preparing J-acid urea of the formula

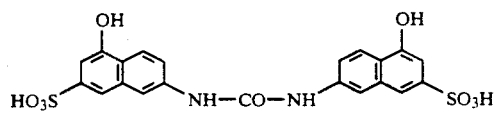

which comprises the steps of:
reacting 7-amino-4-hydroxynaphthalene-2-sulfonic acid (J-acid) of the formula

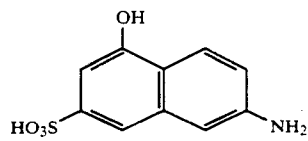

with urea at from 100°-140° C. under a pressure ranging from atmospheric pressure to 10 bar in an inert solvent to form a reaction mixture;
acidifying said reaction mixture to precipitate unreacted J-acid; and
removing said precipitated unreacted J-acid from said reaction mixture.

2. The process of claim 1, further comprising neutralizing said reaction mixture after removal of J-acid to a pH of from 5-8 to precipitate said J-acid urea and isolating said J-acid urea.

3. The process of claim 1, wherein said inert solvent is selected from the group consisting of water, $C_{1-4}$ alkanols, mixtures of water and $C_{1-4}$ alkanols and dilute aqueous mineral acid.

4. The method of claim 1, wherein said reacting step is carried out at from 110°-130° C.

5. The method of claim 1, wherein said reacting step is carried out at a temperature from 115°-125° C.

6. The method of claim 1, wherein said reacting step is carried out at a pressure of from 2-6 bar.

7. The method of claim 1, wherein said reacting step is carried out at a pressure of from 3-5 bar.

8. The method of claim 1, wherein the molar ratio of urea to J-acid in said reacting step is from 1:2 to 4:1.

9. The method of claim 8, wherein the molar ratio of urea to J-acid is about 1:2.

10. The method of claim 1, wherein said removing step comprises filtering.

11. The method of claim 2, wherein said neutralizing step comprises adding 30 -50 wt. % sodium hydroxide or potassium hydroxide solution.

12. The method of claim 2, wherein said isolating step comprises filtering.

* * * * *